(12) United States Patent  
Candy

(10) Patent No.: US 10,583,045 B1  
(45) Date of Patent: Mar. 10, 2020

(54) STRETCHABLE WATERPROOF COMPOSITE MATERIAL AND A METHOD FOR ITS USE

(71) Applicant: Danielle Candy, Middletown, DE (US)

(72) Inventor: Danielle Candy, Middletown, DE (US)

(73) Assignee: AquaCast Liner LLC, Middletown, DE (US)

( * ) Notice: Subject to any disclaimer, the term of this patent is extended or adjusted under 35 U.S.C. 154(b) by 73 days.

(21) Appl. No.: 15/449,879

(22) Filed: Mar. 3, 2017

Related U.S. Application Data

(63) Continuation of application No. 14/339,100, filed on Jul. 23, 2014, now abandoned.

(51) Int. Cl.
| | | |
|---|---|---|
| *A61F 13/04* | (2006.01) | |
| *B32B 3/26* | (2006.01) | |
| *B32B 27/06* | (2006.01) | |
| *A61L 31/14* | (2006.01) | |
| *A61L 31/12* | (2006.01) | |
| *B32B 37/12* | (2006.01) | |
| *B32B 37/18* | (2006.01) | |
| *B32B 38/00* | (2006.01) | |
| *A61F 13/00* | (2006.01) | |
| *B32B 5/18* | (2006.01) | |
| *B32B 7/05* | (2019.01) | |

(52) U.S. Cl.  
CPC ........ *A61F 13/04* (2013.01); *A61F 13/00987* (2013.01); *A61L 31/125* (2013.01); *A61L 31/146* (2013.01); *B32B 3/263* (2013.01); *B32B 5/18* (2013.01); *B32B 7/05* (2019.01); *B32B 27/065* (2013.01); *B32B 37/1284* (2013.01); *B32B 37/185* (2013.01); *B32B 38/0012* (2013.01); *A61L 2430/02* (2013.01); *B32B 2038/0028* (2013.01); *B32B 2250/03* (2013.01); *B32B 2305/022* (2013.01); *B32B 2307/51* (2013.01); *B32B 2307/712* (2013.01); *B32B 2535/00* (2013.01)

(58) Field of Classification Search  
CPC .................................. A61F 13/04; B32B 7/05  
See application file for complete search history.

(56) References Cited

U.S. PATENT DOCUMENTS

| | | | | |
|---|---|---|---|---|
| 3,170,832 A | * | 2/1965 | Shuffman | B29C 44/569 428/159 |
| 2013/0291293 A1 | * | 11/2013 | Jessiman | A43B 1/04 2/459 |

* cited by examiner

*Primary Examiner* — Daniel H Lee  
(74) *Attorney, Agent, or Firm* — Muskin and Farmer LLC

(57) ABSTRACT

A waterproof composite material that comprises three layers, a top layer, a middle layer, and a bottom layer. The middle layer is made of foam while the top layer and bottom layer can be made from a variety of films. The top layer and the bottom layer are formed in a quilted pattern. The top layer and the bottom layer are bunched up (meaning there is extra material there allowing more stretch). A method of manufacturing the waterproof composite material includes placing the three layers on (or in), stretching the middle layer, and then applying a quilt (or other) pattern (using heat and/or pressure) which causes the quilted pattern on the top layer and the bottom layer. The natural contraction of the middle layer (which was stretched when the composite was formed) causes bunching of the top layer and the bottom layer.

6 Claims, 6 Drawing Sheets

STRETCHABLE WATERPROOF COMPOSITE MATERIAL AND A METHOD FOR ITS USE

Application Ser. No. 14/339,100 is incorporated by reference herein in its entirety.

FIELD OF THE INVENTION

The inventive concept relates to a composite material that is both waterproof and stretchable, and a method for manufacture thereof.

BACKGROUND

The use of a cast in the treatment of broken bones has a long history of effectiveness. Traditionally, a layer of cotton cloth is wrapped around the injured limb prior to the application of the plaster or fiberglass cast mixture, in order to keep the skin dry and to create a barrier between the injured person's skin and the cast material. While cotton cloth serves as an adequate barrier, it is known to be water absorbent and difficult to dry when covered with the cast material. A wet cast liner can result in the growth of mold, mildew, and in serious cases, can lead to potentially life-threatening skin infections. Thus, using a cast for fracture treatment requires the injured person to keep the cast as dry as possible, which means cumbersome bathing procedures, and an abstention from any watersport that might result in the immersion of the cast.

Products on the market that provide water resistant or waterproof padding performance include DELTA DRY, PROCEL, ORTHOSKIN, and AQUACAST. However, the construction of these products is such that they do not stretch in the same proportions as a non-waterproof cotton knit material. When applied, the products tend to bunch and wrinkle as they are wrapped around an injured limb, as the average human limb is variable in diameter. This is a reason why orthopedic cast technicians are hesitant to use water resistant materials.

FIG. 1 is a cross section of the prior art padding 50. The prior art padding 50 is comprised of an inner foam 51 covered by outer layers of film 52, 53. The foam 51 and film 52, 53 are both hydrophobic. Adhesives such as the top adhesive layer 54 and bottom adhesive layer 55 are present. Prior art padding also used an adhesive (to help the padding stick to itself when being applied) on one side.

What is needed is a waterproof composite material that allows for stretch in the padding layer.

SUMMARY OF THE INVENTION

It is an aspect of the invention to provide for an improved waterproof composite material.

These together with other aspects and advantages which will be subsequently apparent, reside in the details of construction and operation as more fully hereinafter described and claimed, reference being had to the accompanying drawings forming a part hereof, wherein like numerals refer to like parts throughout.

A BRIEF DESCRIPTION OF THE DRAWINGS

Further features and advantages of the present device, as well as the structure and operation of various embodiments of the present device, will become apparent and more readily appreciated from the following description of the preferred embodiments, taken in conjunction with the accompanying drawings of which:

DETAILED DESCRIPTION

Figure 1:
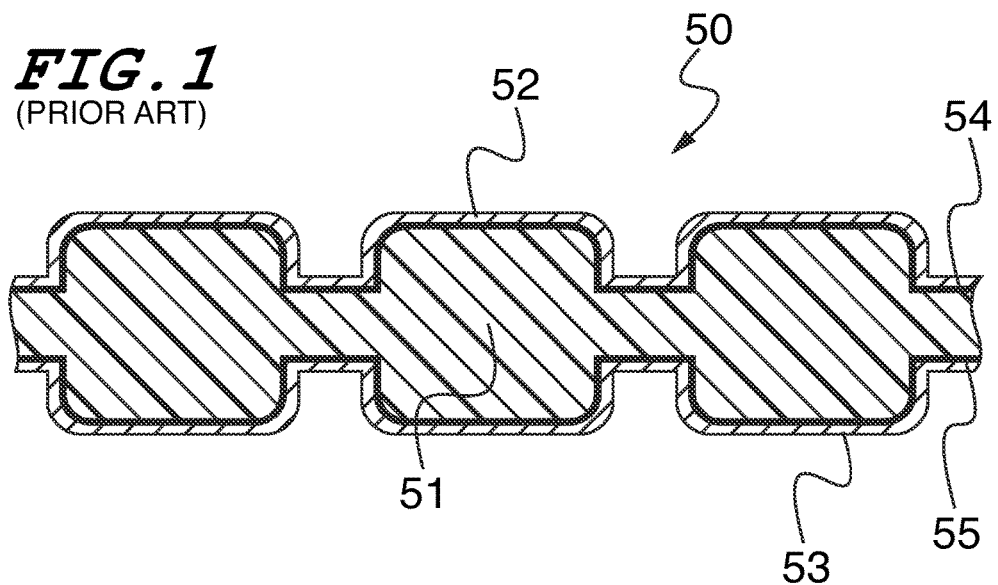
FIG. 1 is a cross section of the prior art.

This description of the exemplary embodiments is intended to be read in connection with the accompanying drawings, which are to be considered part of the entire written description. In the description, relative terms such as "lower," "upper," "horizontal," "vertical," "above," "below," "up," "down," "top," and "bottom," as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," and "interconnected," refer to a relationship wherein structures are secured or attached to one another either directly or indirectly through intervening structures, as well as both movable or rigid attachments or relationships, unless expressly described otherwise. "Hydrophobic" should be construed as meaning not water-permeable, or having quality of being unable to be wetted by water. "Stretch" and "stretchable" should be construed as an increase in length beyond normal length along one or more axes. For example, as used herein, if something is 10% stretchable, stretchable up to 10%, can stretch 10%, can stretch to 10%, can stretch up to 10%, or any similar language, this means that it would stretch (when stretched by a user) a maximum of 10% in excess its ordinary length for that axis (thus 110% of its ordinary length for that axis). This stretch is accomplished without sacrificing any width of the product. In other words, typically when you stretch something in one direction it gets narrower in the transverse direction. The way this product is designed and manufactured, it does not "neck" when it is stretched because of the "bunched up" sections (described herein).

The present inventive concept provides for a waterproof composite material which allows for additional stretching which would allow a technician to apply the material to an injured limb with a minimal amount of wrinkles during application. This should also enhance the material's capacity to channel water out of the cast when drying. Additionally, the added stretch should allow for an overall thinner padding layer with fewer overlaps, leading to higher levels of water vapor transport and evaporation, leading to quicker drying times.

In an embodiment, the invention can comprise a waterproof system that allows for stretch in the padding layer. The stretch can be utilized by an orthopedic cast technician to minimize wrinkles during application of the padding and better conform to a patient's limb. This can enhance the padding material's ability to channel macro water out of the cast, and can lead to reduced drying times. Moisture vapor transport of perspiration or other liquids can be enhanced through the use of a thinner padding layer and a reduction in overlapping wrinkles. Less wrinkles can lead to better air flow through the padding layer and can help improve skin health under a cast.

In an embodiment, the top layer and bottom layer of hydrophobic film can be made using polyester, polyurethane, polytetrafluoroethylene, polyurethane-coated expanded polytetrafluoroethylene (ePTFE), or other materials known in the art. The foam can be made using polyester, polyurethane, acrylic, cotton, wool, organic material or other materials known in the art. These materials can be processed using stress techniques in the foam such that the composite material can stretch up to X % of its normal size under normal tension conditions (e.g., up to two pounds force on a two to four inch wide strip of cast padding). In an embodiment, X can be 34%. In another embodiment X can be any number in the range from 1% to 34% (i.e. less then 35%). In another embodiment, X can be any number in the range 20% to 25%. In another embodiment, X can be any number less than 100%. In another embodiment, X can be any number. The film can be assembled onto both sides of the foam in such manner as to form a quilted pattern that allows for water drainage and air flow between that padding material and the limb.

Figure 2:
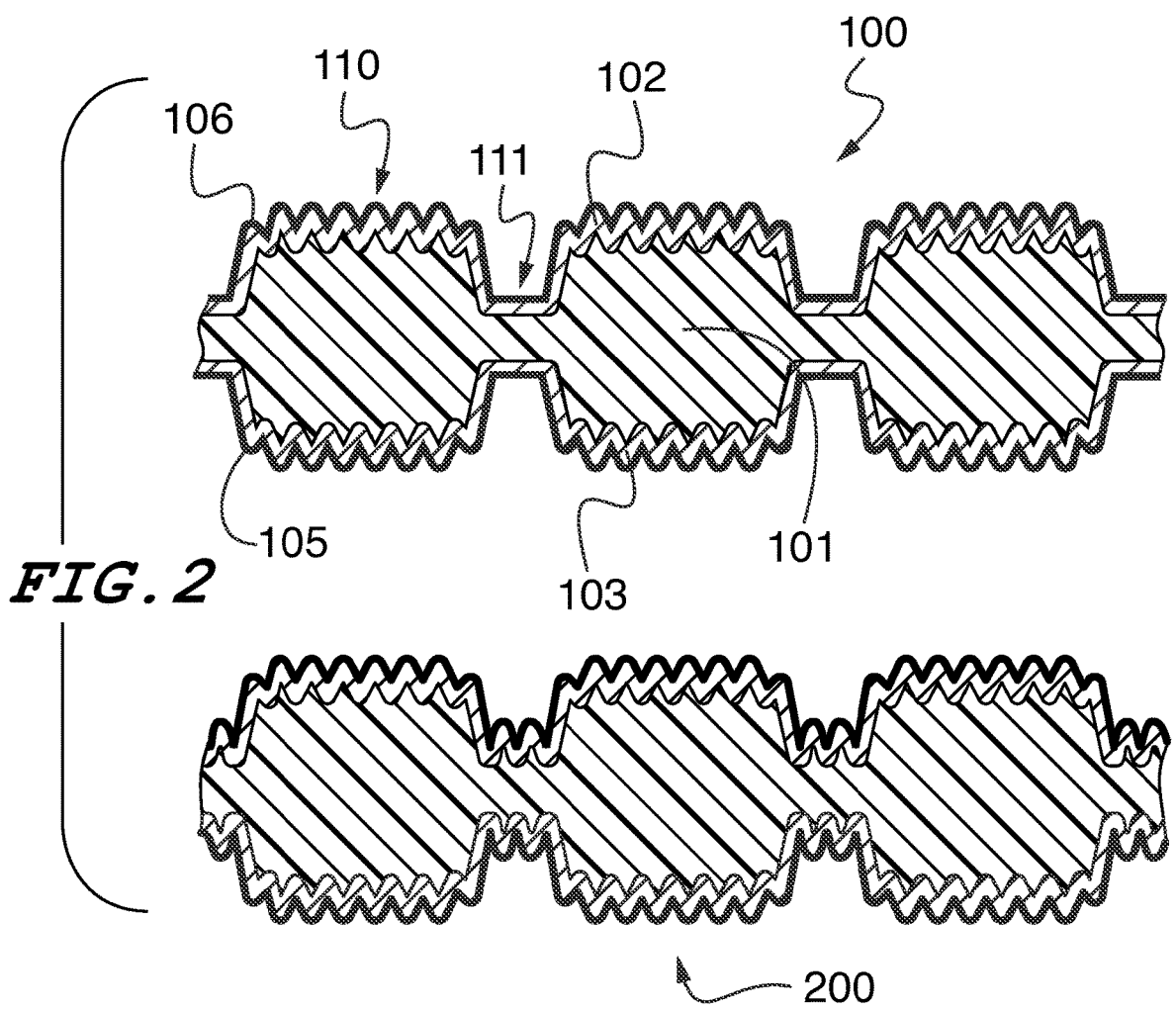
FIG. 2 is a cross section of two example stretchable waterproof composite materials, according to an embodiment.

FIG. 2 is a cross section of two example stretchable waterproof composite materials, according to an embodiment. In an embodiment, a first example of composite material 100 can be formed using a layer of foam 101 bounded by a top layer of hydrophobic film 102 and a bottom layer of hydrophobic film 103. In an embodiment, the top layer 102 and bottom layer 103 of hydrophobic film can be made using polyester, polyurethane, polytetrafluoroethylene, polyurethane-coated expanded polytetrafluoroethylene, or other materials known in the art. The foam 101 can be made using polyester, polyurethane, acrylic, cotton, wool, organic material, or other materials known in the art. In an embodiment, the composite material 100 can be assembled in such a manner as to create a discrete quilted pattern, such that there can exist puffed areas 110 and compressed areas 111. A second example of composite material 200 is the same as the first example 100 (and the same description applies) but also has bunching in the compressed areas (also referred to as land areas). Note that both example composite materials 100, 200 in FIG. 2 have bunching in their puffed areas. Bunching (or "bunched-up") is wrinkling in the top (first) layer and in the bottom (second) layer which provides extra material for stretching. Either of these two example composite materials 100, 200 can be used with any feature(s)/embodiment(s) described herein (anywhere figure number 100 is used it can be replaced with 200 and vice-versa).

In an embodiment, the film used for the top layer and the bottom layer is not elastomeric (meaning the film itself would not stretch) or a thermoplastic. In an embodiment, the film can be a thermoset.

The stretchable waterproof composite material 100 can be formed using the following process. The bottom layer 103 is placed on a lower surface of a forming press (which operates by applying pressure, heat, or both). The foam 101 (such as a polyurethane foam) used for the middle layer is cut to a length shorter than the bottom layer 103 and is stretched to match the length of the bottom layer 103 and placed over the bottom layer 103. The top layer 102 (cut to a same length as the bottom layer 103) is now placed over the foam 101. All three layers at this point are in a flat form. The forming press has a square pattern (e.g., a waffle pattern such as the pattern illustrated in FIG. 3). The forming press is now activated and pressed down into the three layers. The forming pressures applies heavy pressure to all three layers (since the press is in a waffle, quilt, or other pattern only some sections of the material will be compressed by the pressure of the press while other sections will not). The portions of the three layers that are directly pressed by the forming press are compressed and thus the foam in these portions is permanently deformed or crushed thereby forming the compressed areas 111 (fusing the foam to the top and bottom layers), while the areas that are not directly affected by the forming press (because they fall under open parts of the quilt pattern on the press) are the puffed areas 110. The forming press (after it is applied) causes the middle layer to fuse to the top and bottom layers (where the forming press touches the top and bottom layers). Note that because the middle layer of foam 101 was stretched, when it is removed from the press it now naturally retracts and thus causes (by virtue of the foam now being attached to the top layer 102 and bottom layer 103) the top layer 102 and the bottom layer 103 to retract along with the foam 101 thereby causing the bunched appearance visible on the puffed areas 110. Note that in another embodiment, instead of operating by heavy pressure, the press can operate using heat (similar to a hot iron) using the same quilt pattern which can serve to melt the materials and fuse them in a similar fashion to the pressure driven forming press.

For adhesion to itself for ease of application, the bottom layer of hydrophobic film 103 can be coated by a layer of adhesive 105 on the side away from the foam. In an alternate embodiment, the top layer of hydrophobic film 102 can be coated by a layer of adhesive 106 on the side away from the foam. In another embodiment, both the bottom layer 103 can be coated by a layer of adhesive 105 on the side away from the foam and the top layer 102 can be coated by a layer of adhesive 106 on the side away from the foam. Coating either or both layers in this manner will help the composite material stick when wrapped around itself (such as when used as a cast or bandage). The adhesive used can be any biocompatible pressure sensitive adhesive, such as those available from DOW CORNING such as MG 7-9900 A&B.

Note that the top layer 102 can also be referred to as a first layer, and the bottom layer 103 can also be referred to as a second layer, and vice-versa.

Note that the bunched up portions 102 of the top layer and the bottom layer 103 provide extra film (or whatever material is being used for the top layer and the bottom layer) so that when the material is stretched, the bunched up portions unfold thereby providing the extra film to accommodate the stretch.

Note that the composite material can be made of any length and width. In one embodiment, the length can be 1 to 20 feet long or longer. The composite material can be rolled up in a roll for convenient storage. The composite material can also be made of any width (for example, 1 inch to 2 feet wide, such as 2 inches wide, 3 inches wide, 4 inches wide, 6 inches wide). The composite material can also be formed in a square (e.g., 18 inch square).

Figure 3:
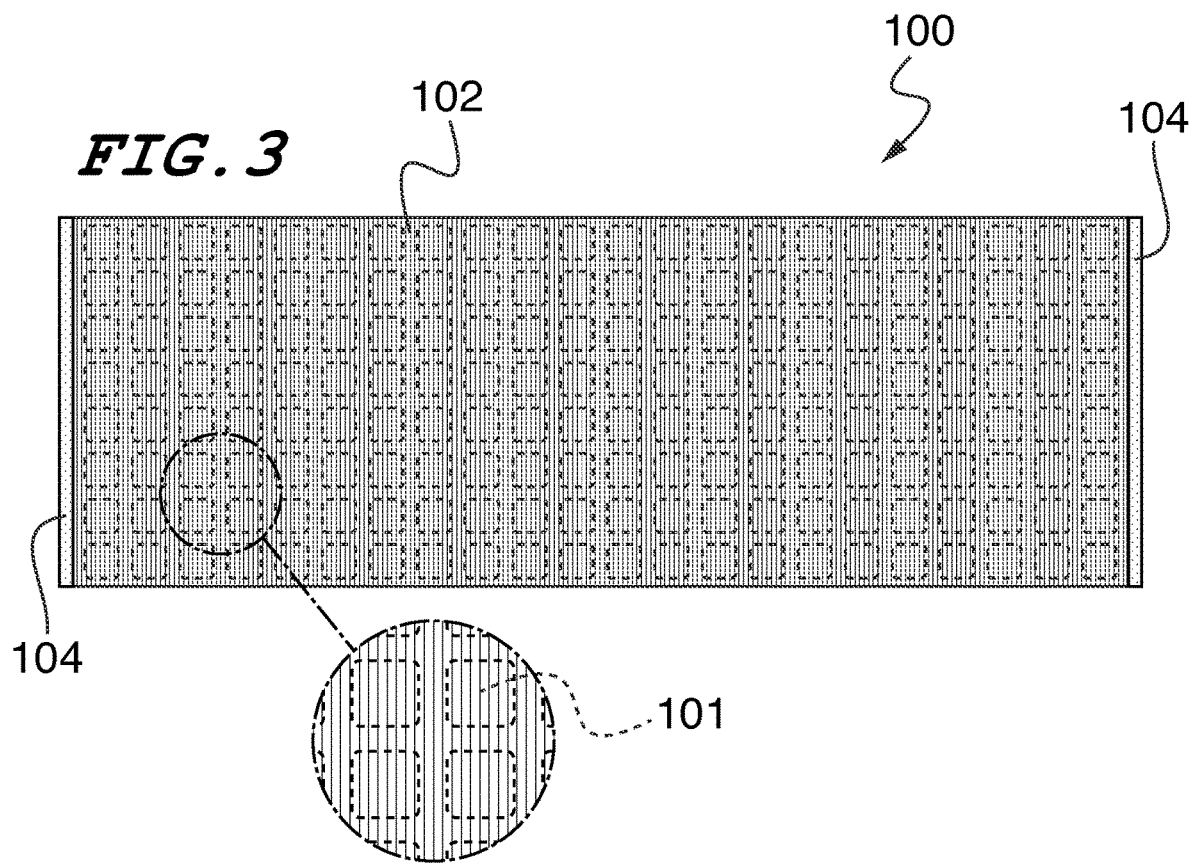
FIG. 3 is a top view of the stretchable waterproof composite material, according to an embodiment.

FIG. 3 is a top view of the stretchable waterproof composite material 100, according to an embodiment. In an embodiment, the composite material 100 can be formed using a layer of foam 101 bounded by a top layer of hydrophobic film 102 and a bottom layer of hydrophobic film (not shown). In an embodiment, the top layer 102 and bottom layer (not shown) of hydrophobic film can be made using polyurethane, polytetrafluoroethylene, polyurethane-coated expanded polytetrafluoroethylene (ePTFE), or other materials known in the art. The foam 101 can be made using polyester, polyurethane, acrylic, cotton, wool, organic material, or other materials known in the art. In an embodiment, the foam 101 layer can be compressed in such a way as to form a quilt pattern throughout the composite material 100. In an alternate embodiment, the ends of the material can comprise an adhesive 104 such that the composite material 100 can adhere to itself for ease of application.

Figure 4:
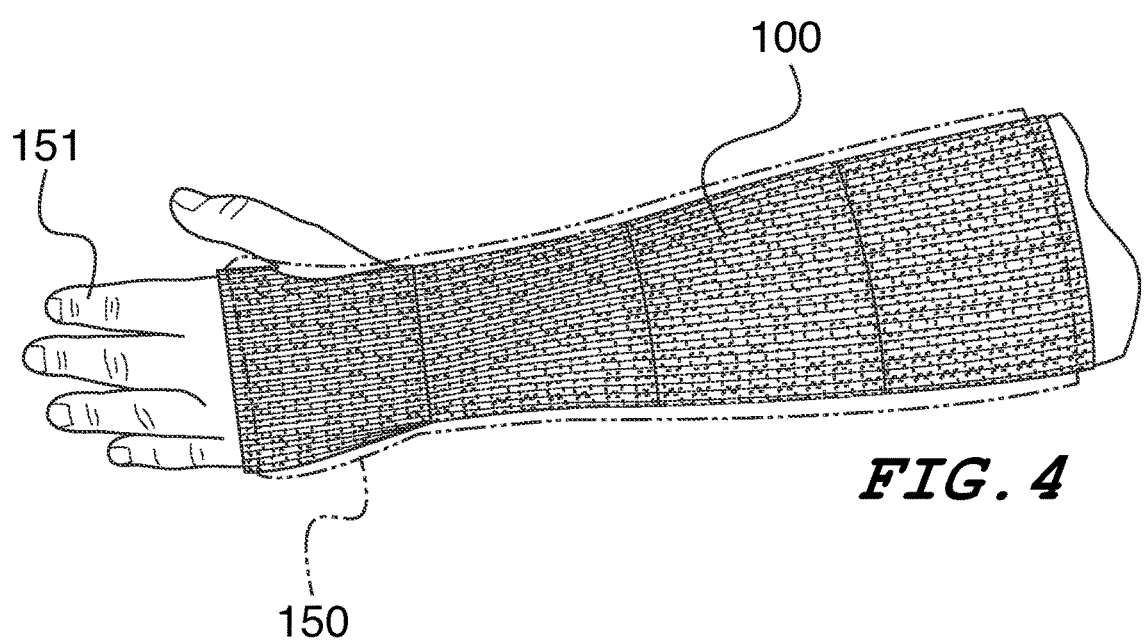
FIG. 4 is a view of the stretchable waterproof composite material applied to a human limb, according to an embodiment.

FIG. 4 is a view of the stretchable waterproof composite material 100 applied to a human limb 151, according to an embodiment. In an embodiment, the composite material 100 is wrapped around a human limb 151 such that it can cover slightly more than the entire area covered by an orthopedic cast 150.

As an alternative to using foam 101 in the middle layer, the middle layer can be formed using bubble wrap which comprises plastic which will melt and adhere to the top and bottom layers when pressed Thus, in this embodiment, after being pressed, there is no middle layer but for air. In another embodiment, molds using a vacuum are used with no foam, bubble wrap, or other middle layer.

Figure 5:
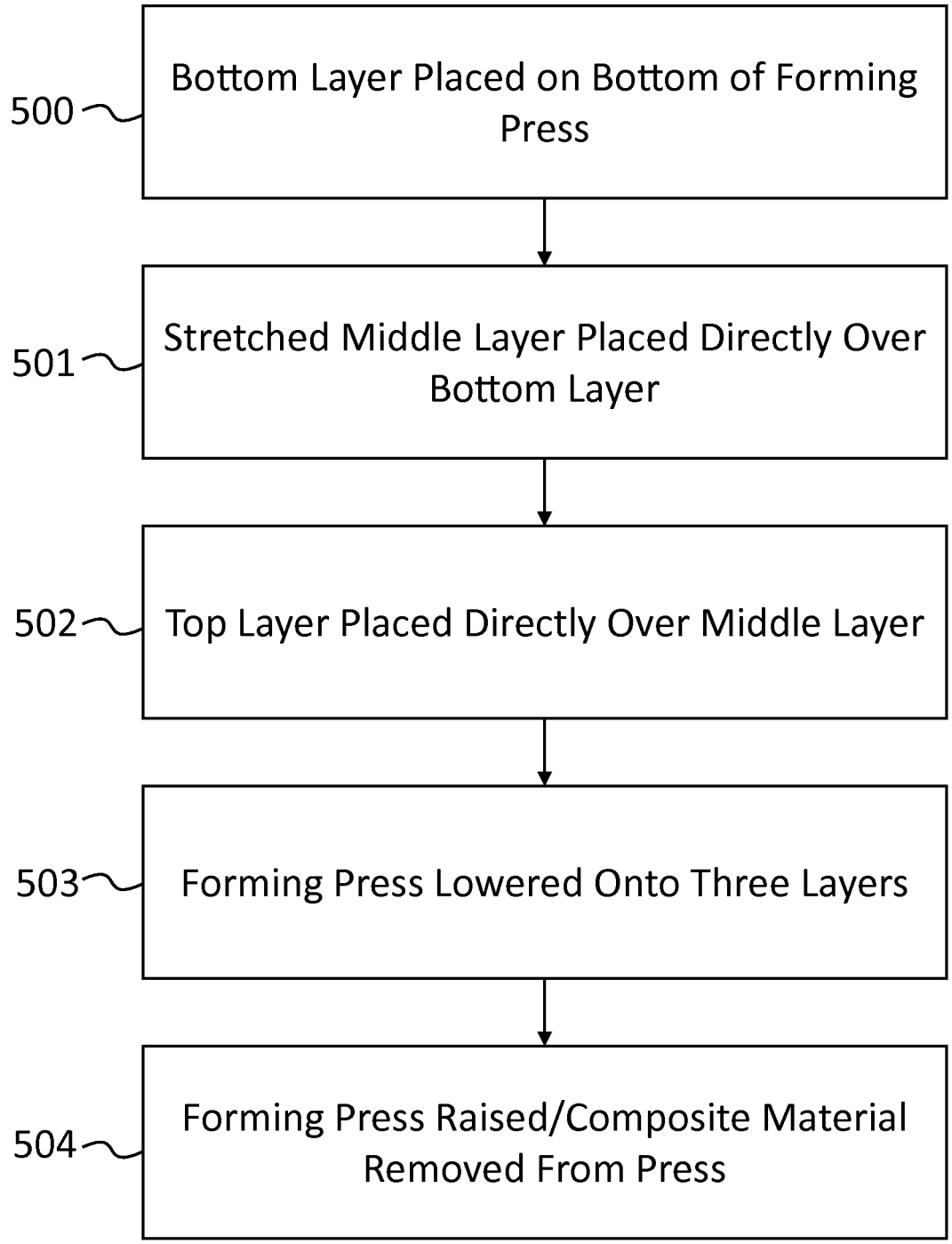
FIG. 5 is a flowchart illustrating an exemplary method of forming a waterproof composite material, according to an embodiment.

FIG. 5 is a flowchart illustrating an exemplary method of forming a waterproof composite material, according to an embodiment.

The method starts in operation 500, wherein a bottom layer 103 is placed on a bottom of a forming press. The press uses a waffle (or quilt) shape piece of metal on top that matches with another waffle (or quilt) shape piece of metal on the bottom of some other pad that deforms into against the "mold" (hollow areas between the top and bottom pieces of metal). It can be a hydraulic, electric or pneumatic or any other kind of machine that can apply pressure to the materials. Additionally, it could be a rotary "mold" that forms the shape as it "rolls" over the materials. The bottom layer can be a rectangular piece of film (such as any material described herein). All three layers are placed between the top piece of metal and the bottom piece of metal of the forming press, so the press applies pressure to both the top and bottom layers when activated.

The method then proceeds to operation 501, where a foam 101 middle layer (currently in flat form, either rectangular or fed from a roll) is placed directly over the bottom layer 103. The middle layer would be stretched Y % of its natural size/length (in order words exceeds its natural length by Y %) when the composite material is made in the forming press. For example, if Y is 50%, then a one foot long middle layer would stretch to 1.5 feet (50% longer). Y can be any number from 10% to 90%. In an embodiment, Y can be from 20% to 30%. In another embodiment Y can be 50%. In another embodiment, Y can be 100% (in other words, the foam would be stretched to twice its length when fused to the top and bottom layers. In another embodiment, Y can be at least 20%. In another embodiment, Y can be at least 50%. In another embodiment, Y can be at least 70%. In another embodiment, Y can be from 70% to 100%. In another embodiment, Y can be from 10% to 100%. In another embodiment, Y can be from 20% to 30%. In another embodiment, Y can be from 40% to 50%. In another embodiment, Y can be up to 100% (including 100%).

Note that previously described was X % which is how much the composite material (after being formed) would stretch (in excess of its natural length). Y % is how much the middle layer is stretched when the composite material is formed. While intuitively one might think X and Y would be the same, this is typically not the case. In some cases (due to an effect known as hysteresis), the middle layer has to be stretched at a higher amount (when the material is formed in the press) to get a lesser amount of potential stretch in the finished composite material (in other words Y>X).

The foam 101 would typically have the same width as the bottom layer 103. In one embodiment, the foam 101 can be stretched (e.g., a tension force is applied) and held into place using a grip vice on each end of the form 101. In an embodiment, the forming is a continuous process, so there is a roll for the middle layer (e.g., foam) at each end with the rolls of foam positioned such that tension between the rolls stretches the material. The top and bottom layers would also have rolls, and the three layers (top layer, middle layer under tension, bottom layer) would be pulled through the forming press periodically using the rolls so at predetermined lengths, the forming press would be applied. Unlike the middle layer, the top and bottom layers are not stretched when the composite material is formed in the forming press.

From operation 501, the method proceeds to operation 502, wherein the top layer 102 is placed directly over the foam 101 middle layer. The top layer 102 would typically have the same dimensions as the bottom layer 103.

From operation 502, the method proceeds to operation 503, wherein the forming press is activated (lowered) onto the three layers. The forming press can have a quilted pattern (although other patterns can be used such as squares, dashes, rectangles, lines, octagons, dots, or other shapes) which creates the pattern of squares with recessed borders around them (illustrated in FIG. 3). The forming press may be hot and when applied to the three layers, the pressure and heat will form the foam in the portions directly below where the forming press comes into direct contact with the top layer 102. The foam will be compressed, causing the thinner areas 111. The foam 101 (after being pressed) may also serving as an adhesive thereby bonding the top layer 102 to the foam and the bottom layer 103 to the foam 101. Note that the forming press can operate using only pressure (no heat), only heat (no pressure) or both.

From operation 503, the method can proceed to operation 504, wherein the composite material (now all bonded together) is removed from the forming press. The tool using to stretch the foam layer 101 is loosened thereby releasing the foam layer 101 (thus the tension force applied to the foam layer 101 is now released). Once released, the foam layer 101 will contract (since it was already in a stretched state when the composite material was formed) thereby causing the top layer 102 and the bottom layer 103 to contract with it (since the top layer 102 and the bottom layer 103) are now integrated to the foam layer 101. This contraction causes the top layer 102 and the bottom layer 103 to "bunch up" as illustrated in FIG. 2. An adhesive can optionally be added to top layer 102, bottom layer 103, or both. The adhesive assists the composite material to form a tight seal when applied to a person.

The quilting provides for the fastening together of the layers and allows for the material to channel liquid water out of the cast liner and away from the wearer. The bunched up portion provides additional film so that when the material stretches it does not shrink in the axis perpendicular to the direction of stretch, in other words it does not "neck."

Figure 6:
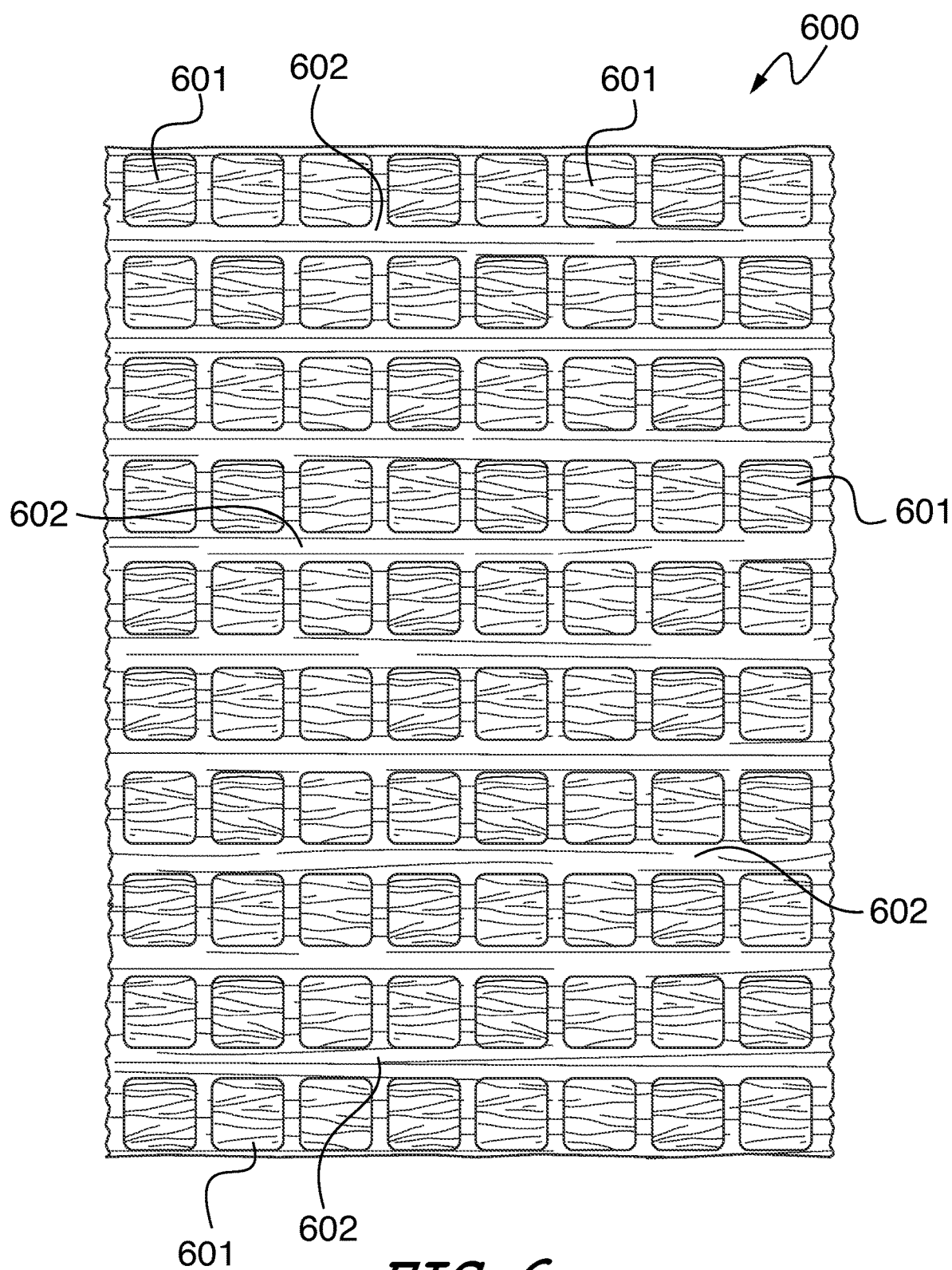
FIG. 6 is a top view of a waterproof composite material, according to an embodiment.

FIG. 6 is a top view of a waterproof composite material, according to an embodiment.

The waterproof composite material 600 bunches up in both the puffed up areas 601 and the compressed areas 602.

Figure 7:
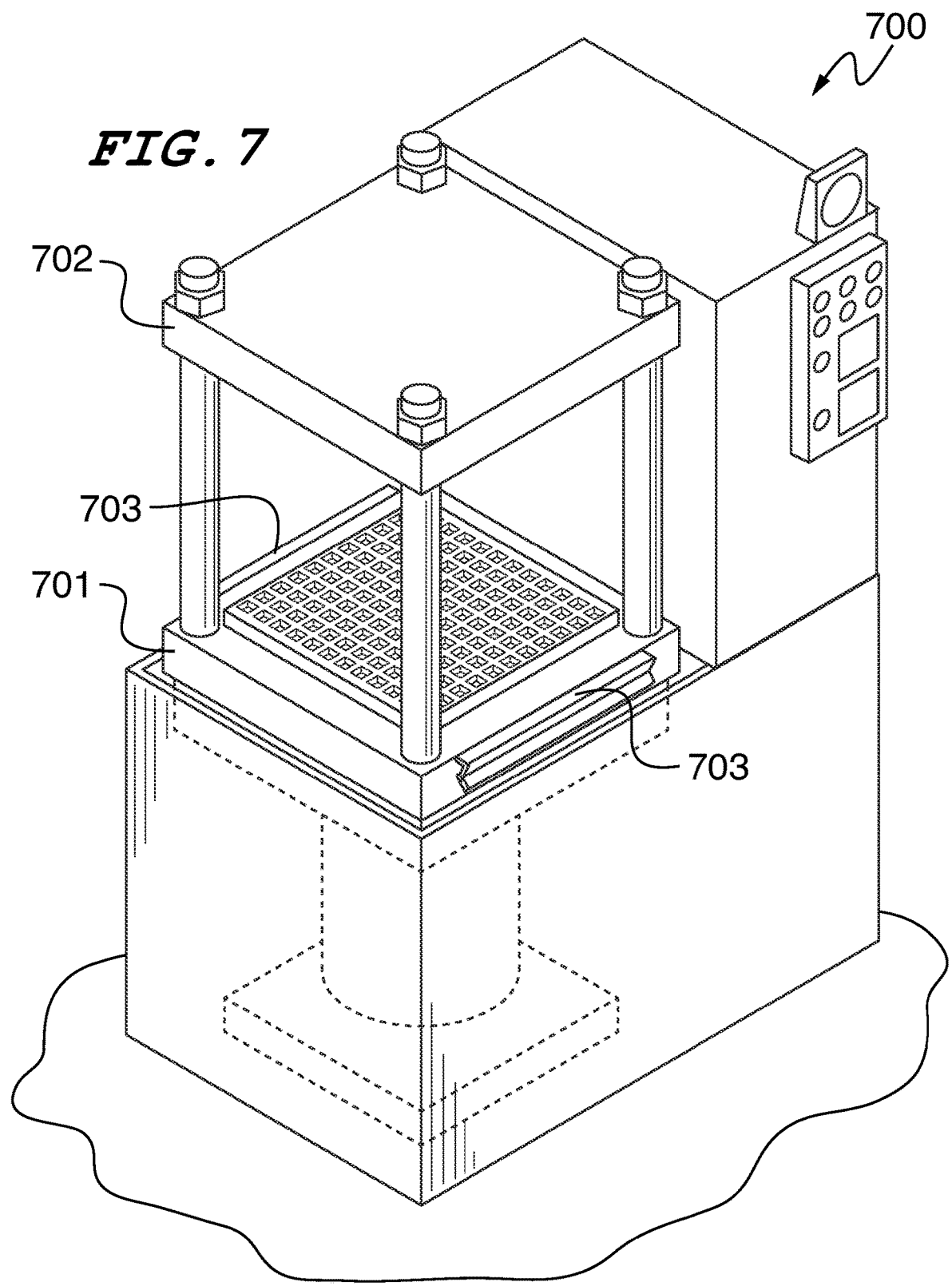
FIG. 7 is a perspective view of a press that can be used to form a waterproof composite material, according to an embodiment.

FIG. 7 is a perspective view of a press that can be used to form a waterproof composite material, according to an embodiment.

A press 700 can be forming press that operates by pressure, or by heat, or by a combination of pressure and heat. The press can be pneumatic which operates (exerts pressure) on all four posts. The press can be any size such as one foot square. The bottom plate 701 remains fixed and the top plate 702 moves vertically and when it is lowered exerts pressure (using motors, hydraulics, etc.) on the material placed on the bottom plate 701. The bottom plate 701 and the top plate 702 both have a pattern (such as a waffle, square, quilt, etc.) so that the compressed areas are where the top pattern and the bottom pattern meet and the puffed up areas are where there is no pressure exerted on the material due to the cooperating pattern on both the top plate 702 and the bottom plate 701.

In an embodiment, a strip of the second layer is placed on the bottom plate 701, the middle layer is placed above the bottom layer, and then the first layer is placed on top of the middle layer. The middle layer is stretched (as described herein). Grips such as a vise (or clips such as binder clips which can be an industrial strength binder clip) or tension clips 703 can be used to hold the middle layer in place so that it is kept under tension (stretched). Both tension clips 703 are identical and operate in a same manner as a clip on a clipboard (pressing the bottom of each clip 703 opens the clip 703 and after the middle layer is positioned inside each clip the clip will then naturally snap back thereby securing the middle layer). After the press is operated (lowered) and the composite material formed, then the composite material can be removed from the press and the process can be repeated. Note that a number of strips of composite material can be made simultaneously (side by side) in the press each time (e.g., 2-5 or more at the same time)

If the press is one foot square, then if one foot of material is used for the top (first) layer, middle layer, and bottom (second) layer, then the final composite material made would actually be shorter than one foot long. This is because once removed from the press (and clips holding the middle layer under tension), the middle layer would contract backs to its natural length thereby reducing the length of the composite material to less than one foot. For example, if the middle layer was stretched (increased) 50% of its natural length to a one foot strip (and the top and bottom layers of film were also cut to be one foot strips), then the length of the final product would be approximately ⅔ of a foot (because the middle layer would require only ⅔ of a foot to stretch out to one foot).

Note that the bottom plate 701 and the top plate 702 can both have the pattern embedded on them. The patterns on plate plates cooperate, in other words, each pattern has an extending portion and a recessed portion, and when the press is closed (assuming no article in between both plates) the extending portions of each pattern on each plate touch while the recessed portions of each plate do not touch. The compressed portions of the composite material are formed where the patterns (top and bottom) are extended (thereby exerting pressure on the materials) while the puffed-up areas are formed where the patterns (top and bottom) are recessed (providing a space for the material so it is not under pressure). The embodiments described herein assume that the pattern is present on both sides of the press (top plate 701 and bottom plate 702). In an alternate embodiment, the pattern can only be embedded on the bottom plate 701 or the top plate 702 but not both.

The composite material can be made using a manual process as follows. The three layers are separate strips of the respective material placed inside the press (with the middle layer being under tension as described herein). The press is lowered under pressure (or heat or both), thereby forming the composite material as described herein. The press can then be raised and the finished material removed from the press 800. This process can be repeated.

Figure 8:
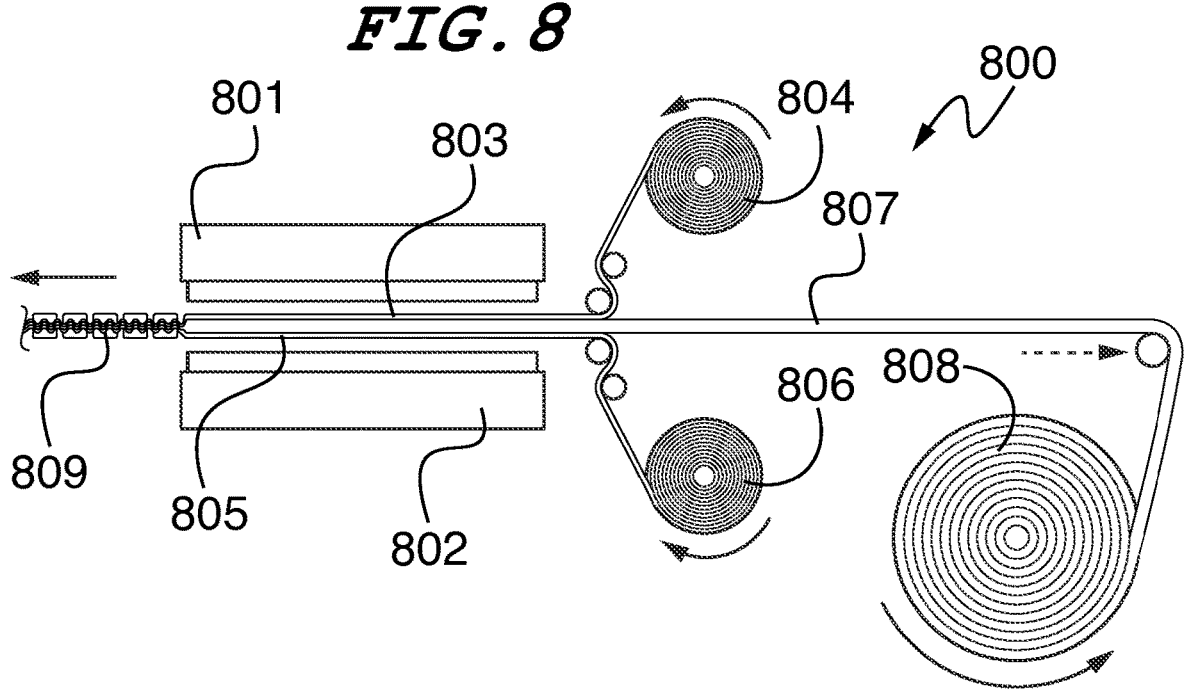
FIG. 8 is a side view of a system that can be used to form a waterproof composite material using a flat press, according to an embodiment.

FIG. 8 is a side view of a system that can be used to form a waterproof composite material using a flat press, according to an embodiment. The system illustrated in FIG. 8 can be automated and can continuously form a roll of the composite material without breaks in the composite material formed.

The press 800 can be a flat forming press such as illustrated in FIG. 7. A top plate 801 and a bottom plate 802 are used. A first (top) layer 803 comes of a first (top) layer roll 804. A second (bottom) layer 805 comes off a second (bottom) layer roll 806. A middle layer 807 comes off a middle layer roll 808.

Once all three layers are inside the press (with the middle layer being under tension as described herein), the press can be activated (lowered all the way down) and then raised. The composite material 809 (the finished product after pressing) is then pulled out of the press and can be rolled into a roll (not pictured) while new material is being pulled off the first layer roll 804, second layer roll 806, and middle layer roll 808. The process can be repeated until a roll of desired length is formed, upon which the composite material can be cut so a new roll of composite material can be formed.

Figure 9:
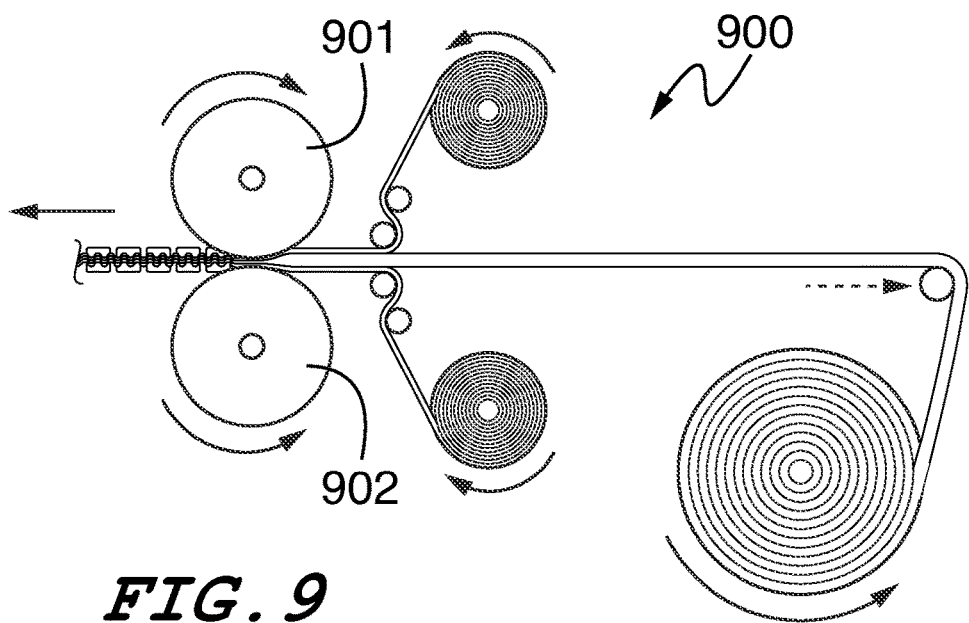
FIG. 9 is a side view of a system that can be used to form a waterproof composite material using a circular press, according to an embodiment.

FIG. 9 is a side view of a system that can be used to form a waterproof composite material using a circular press, according to an embodiment.

FIG. 9 is the same as FIG. 8 but instead uses a rotating press 900 that utilizes two cooperating rolling cylinders (or other circular shape). A top cylinder 901 and a bottom cylinder 902 both have patterns embedded on each that cooperate in the same manner as the flat press described herein. One advantage to using the configuration illustrated in FIG. 9 is that the rotating press can operate continuously, and thus obviate the need to start and stop the flat press from FIG. 8.

While the composite material described herein has been described as being waterproof, in a further embodiment, the composite material does not have to be waterproof.

Although the present apparatus has been described in terms of exemplary embodiments, none is limited thereto. Rather, the appended claims should be construed broadly, to include other variants and embodiments of the present apparatus, which may be made by those skilled in the art without departing from the scope and range of equivalents of either the apparatus or the methods for using such an apparatus.

What is claimed is:

1. A method of manufacturing a composite material, the method comprising:
   providing a top layer of film;
   providing a bottom layer of film;

providing a middle layer of foam between the top layer and the bottom layer;

stretching the middle layer past a natural length of the middle layer;

applying a press with a pattern onto the top layer and bottom layer while the middle layer is stretched past the natural length, thereby creating the composite material, thereby causing a contraction of the middle layer causing bunching on the top layer and the bottom layer.

2. The method as recited in claim 1, wherein the top layer of film is hydrophobic.

3. The method as recited in claim 2, wherein the bottom layer of film is hydrophobic.

4. The method as recited in claim 1, wherein the top layer of film and the bottom layer of film are polyurethane coated expanded polytetrafluoroethylene.

5. The method as recited in claim 1, further comprising applying an adhesive to the top layer.

6. The method as recited in claim 1, wherein the stretching the middle layer stretches the middle layer up to 100% in excess of the natural length.

\* \* \* \* \*